(12) United States Patent
Banning et al.

(10) Patent No.: US 6,395,307 B1
(45) Date of Patent: May 28, 2002

(54) POURABLE ALGINATE COMPOSITIONS

(75) Inventors: Douglas Banning, London; Peter William Dettmar, Patrington; Ian Gordon Jolliffe, Cottingham; Frank Chadwick Hampson, Hedon, all of (GB); Edvar Jarle Onsoyen, Drammen (NO); Paul Frederick Field, Hull (GB); Duncan Quinell MacKenzie Craig, Belfast (IE); Ase Hanne Kristensen, Oslo (NO)

(73) Assignee: Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 09/403,217

(22) PCT Filed: Apr. 23, 1998

(86) PCT No.: PCT/GB98/01188

§ 371 (c)(1),
(2), (4) Date: Dec. 17, 1999

(87) PCT Pub. No.: WO98/48814

PCT Pub. Date: Nov. 5, 1998

(30) Foreign Application Priority Data

Apr. 30, 1997 (GB) .............................................. 9708772
Apr. 30, 1997 (GB) .............................................. 9708773

(51) Int. Cl.[7] ..................... A61K 33/00; A61K 31/715; A61K 31/734; A61K 47/02; A61K 47/36
(52) U.S. Cl. ...................... 424/717; 424/722; 514/54; 514/769; 514/779; 514/925; 514/927
(58) Field of Search ................................ 424/682, 686, 424/687, 722, 715, 717; 514/779, 925, 927, 54, 769

(56) References Cited

U.S. PATENT DOCUMENTS

| | | | | |
|---|---|---|---|---|
| 4,172,120 A | * | 10/1979 | Todd et al. ................... | 424/44 |
| 4,744,986 A | * | 5/1988 | Luber et al. ................. | 424/686 |
| 4,869,902 A | * | 9/1989 | Buehler et al. ............. | 424/686 |
| 5,286,492 A | * | 2/1994 | Dettmar et al. ............. | 424/458 |
| 5,681,827 A | * | 10/1997 | Field ........................... | 514/54 |
| 5,888,540 A | * | 3/1999 | Sugden et al. ............... | 424/455 |

FOREIGN PATENT DOCUMENTS

| | | | |
|---|---|---|---|
| EP | 0059221 | * | 9/1982 |
| EP | 0.286085 | * | 7/1992 |
| EP | 0 586 260 | * | 3/1994 |
| GB | 1 524 740 | | 9/1978 |
| GB | 2 298 365 | | 9/1996 |
| JP | 57-46920 | | 3/1982 |
| WO | WO85/04806 | | 11/1985 |
| WO | WO88/00825 | * | 2/1988 |

OTHER PUBLICATIONS

Copy of Examination Report for GB 9808522.8 dated Jul. 17, 1998.*

Copy of Examination Report for GB 9808547.5 date Jul. 17, 1998.*

PCT International Search Report for PCT Application No. PCT/GB98/01188 dated Jul. 15, 1998.

* cited by examiner

Primary Examiner—Jose' G. Dees
Assistant Examiner—Frank Choi
(74) Attorney, Agent, or Firm—Fish & Richardson P.C.

(57) ABSTRACT

An aqueous pourable liquid composition comprising a high concentration of sodium alginate and an alkali metal bicarbonate, wherein the sodium alginate has an average mannuronic acid residue to guluronic acid residue ratio of at least 0.6:1. In addition, an alginate or alginic acid for forming a protective coating on gastrointestinal mucosal tissue, use of and compositions including the same are provided.

19 Claims, No Drawings

POURABLE ALGINATE COMPOSITIONS

This application is a 371 of PCT/GB98/01188, filed Apr. 23, 1998.

FIELD OF THE INVENTION

The present invention relates to compositions including alginates or alginic acid, to their preparation and in particular to the use of such compositions for the treatment of reflux oesophagitis, gastritis, dyspepsia or peptic ulceration and also to the use of such compositions as targeted delivery and/or sustained release compositions.

The present invention further relates to the preparation of pourable liquid sodium alginate compositions and in particular to the preparation of such compositions for the treatment of reflux oesophagitis, gastritis, dyspepsia or peptic ulceration, or for use as sustained releasing or targeted delivery compositions.

BACKGROUND OF THE INVENTION

Alginates may be found in and isolated from various species, in particular from algae belonging to the order Phaeophyceae and soil bacteria such as *Azotobacter vinelandii* and *Azotobacter crococcum* and from several strains of Pseudomonas bacteria. Common algal sources of alginates include *Laminaria digitata, Ecklonia maxima, Macrocystis pyrifera, Lessonia nigrescens, Ascophyllum nodosum, Laminaria japonica, Durvillea antartica, Durvillea potatorum* and *Laminaria hyperborea*.

Alginates are salts of alginic acid which is a linear hetero-polysaccharide comprising units of β-D-mannuronic acid (denominated M units) and α-L-guluronic acid (denominated G units).

Alginic acid and alginates may comprise homopolymeric sequences of mannuronic acid, known as M blocks, homopolymeric sequences of guluronic acid, known as G blocks and mixed sequences of mannuronic acid and guluronic acid units, known as MG blocks or alternating blocks. A hypothetical schematic representation of the structure of a typical alginate chain is represented below:

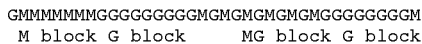

Usually, alginates will contain all three different blocks and each block will contain from about three to about twenty monomer (M or G) units. The distribution of the M, G and MG blocks and also the relative quantity of the M and G units varies according to the species from which the alginate is isolated and in the case of larger plants, on the part of the plant (e.g. stem or leaf) from which the alginate is isolated.

Alginates are also used in various other products such as, for example, food, dental products and cosmetics. The alginates are particularly useful in these areas as gelling, thickening, stabilising, swelling and viscosity imparting agents. The particular alginates used can be selected according to their particular properties which can depend on the distribution of the M blocks, G blocks and MG blocks and the relative quantities of the M and G monomer units.

Reflux oesophagitis occurs when small amounts of gastric juice, food and/or bile acids pass into the lower part of the oesophagus and cause oesophageal inflammation accompanied by pain which may manifest itself in the form of heartburn.

One approach to the problem of reflux oesophagitis has been to administer a preparation which on contact with gastric acid generates a carbonated gelatinous foam or raft which floats on the stomach contents. When reflux occurs it is this raft which precedes the stomach contents into the oesophagus, thus protecting the mucosa from further irritation. Known preparations of this type include solid preparations in the form of powder or tablets containing alginic acid, sodium bicarbonate and antacid materials; or liquid preparations containing sodium alginate, sodium bicarbonate and calcium carbonate marketed under the name GAVISCON™ (Reckitt & Colman Products Ltd). In our British Patent No. 1524740 we describe such liquid preparations.

A current problem with liquid alginate products of the above type is the size of the dose which must be taken (up to 20 ml four times daily). This results in large volumes of products which are not conveniently portable and which take up a lot of space in pharmacies, warehouses etc.

It is therefore an aim of the present invention to provide more concentrated products thereby reducing the relative dosage volume.

On the one hand, we have found that merely doubling the concentration of all ingredients in conventional sodium alginate compositions leads to compositions which are too thick to dispense from a bottle and may even be too thick to comfortably swallow.

On the other hand, we have found that partially reducing the sodium bicarbonate concentrations in such products will reduce the initial viscosity to apparently acceptable levels at which pouring may be achieved. However if the bicarbonate concentrations are reduced too far there will be inadequate carbon dioxide production in the stomach, which will lead to inadequate raft formation.

We have found moreover that compositions having high concentrations of conventional sodium alginates and low concentrations of sodium bicarbonate have a second serious defect, i.e. their pouring properties are irreversibly lost if storage temperatures drop too low. Specifically, if such compositions are stored at below 5° C. for 48 hours or more they will remain too thick to pour, even after being restored to room temperature and vigorously shaken. Temperatures of 5° C. or lower are commonly encountered when commercial products are stored for long periods in warehouses or transported over long distances.

Another approach proposed for the treatment of oesophageal and gastric disorders has been to use a material which provides a protective coating on the mucus or mucosa of the gastrointestinal tract.

Materials proposed as such mucoprotectants or bioadhesives have included the antacid sucralfate and various polymers such as polyacrylates, cross linked polyacrylates (for example, the Carbopols and Polycarbophil from the B. F. Goodrich company), sodium carboxymethylcellulose and chitosans.

Alginates have not been generally accepted as bioadhesives and this may be due either to the many different methods employed for bioadhesion or, as the present inventors now believe, to the use of poorly characterised alginates.

Accordingly, with respect to the aim of the present invention to provide more concentrated products thereby reducing the relative dosage volume, a need exists for an aqueous pourable liquid composition comprising a high concentration of sodium alginate and an alkali metal bicarbonate, to thereby provide a more concentrated product having a reduced relative dosage volume.

With respect to the bioadhesion of alginates, a further need exists for an alginate or alginic acid for forming an effective protective coating on gastrointestinal mucosa when brought into contact with same, which has hereto before not been achievable.

SUMMARY AND DETAILED DISCLOSURE OF THE INVENTION

The inventors have now unexpectedly found that the thickening problems relating to the pourable product may be alleviated by using particular forms of sodium alginate.

Sodium alginate mainly comprises the sodium salt of alginic acid which is a mixture of polyuronic acids composed of residues of D-mannuronic and L-guluronic acids as previously described. It may be obtained from algae belonging to the order Phaeophycae.

Generally alginates having high proportions of guluronic acid resides have been preferred in prior art liquid alginate products. Typically materials having mannuronic to guluronic acid residue ratios of approximately 0.4:1 (i.e. 4 mannuronic acid residues to 10 guluronic acid residues) have been used.

In the compositions described above for the treatment of reflux oesophagitis it has been considered important to form a gelatinous carbonated foam or raft of the highest strength. An important factor in the raft strength has been the cross-linking of the alginates through the presence of a polyvalent ion, such as through the inclusion of calcium carbonate in the above described composition.

Cross-linking via the polyvalent ion occurs to the greatest extent between the guluronic acid residues in the alginate chains and for this reason raft-forming compositions of the above described type have comprised alginates rich in G units. These are also known as "high G" alginates. (Similarly alginates rich in M units are known as "high M" alginates.) Typically, the high G alginates will have a mannuronic acid residue to guluronic acid residue ratio (hereinafter M/G value) of 2/3 or less.

The inventors have now surprisingly found that the thickening problems described above may be alleviated by using sodium alginates having higher mannuronic acid residue to guluronic acid residue ratios than have previously been used in liquid products.

Therefore, according to a first aspect to the present invention there is provided an aqueous pourable liquid composition comprising a high concentration of sodium alginate and an alkali metal bicarbonate, wherein the sodium alginate has an average mannuronic acid residue to guluronic acid residue ratio of at least 0.6:1. Such compositions are preferably suitable for use as pharmaceutical compositions.

Such compositions are pourable at room temperatures, and furthermore this property is regained upon warming following prolonged storage below 5° C. for up to six weeks or more (although reasonably vigorous shaking may be required).

By pourable we mean that the compositions of the invention will flow evenly at room temperature (possibly following reasonably vigorous shaking) such that doses of, for example, 5 ml may be measured out with reasonable accuracy. For example reproducible doses of as low as 5 ml may be dispensed from screw cap bottles having neck diameters of 1.5 cm, or from squeezable plastic bottles having dispensing outlets as small as 5 mm diameter.

It is known that increasing the mannuronic acid residue content of sodium alginate may cause a reduction in the coherence of the rafts produced by raft forming preparations on contact with gastric acid. Therefore a balance must preferably be struck between increasing the mannuronic acid residue content of the sodium alginate to reduce the thickening problems, but not increasing it to such an extent that effective rafts are not produced in the stomach.

Therefore in the compositions of the invention the average ratio of mannuronic acid residues to guluronic acid residues in the sodium alginate is preferably 0.65:1 to 3:1, more preferably 0.65:1 to 1.5:1, most preferably 0.7:1 to 1.3:1 and especially 0.75:1 to 1.1:1.

The sodium alginate used in the compositions of the invention may comprise materials from the same source all having approximately the same mannuronic to guluronic acid residue ratios or, preferably, it is a blend of materials having different mannuronic to guluronic acid residue ratios. Preferably at least 50% of the sodium alginate has a mannuronic to guluronic acid residue ratio of greater than 0.8:1.

Most preferably at least 70% of the sodium alginate has a mannuronic to guluronic acid residue ratio greater than 0.9:1.

Especially preferred are compositions of the invention which comprise a mixture of sodium alginates wherein 70 to 80% of the sodium alginate has a mannuronic to guluronic acid residue ratio of from 0.9:1 to 1.2:1, and 30 to 20% of the sodium alginate has a mannuronic to guluronic acid residue ratio of from 0.35:1 to 0.5:1.

Alginates having average mannuronic to guluronic acid residues ratios of greater than 0.6:1 may be extracted from many sources, for example from *Laminaria digitata, Ecklonia maxima, Macrocystis pyrifera, Lessonia nigrescens, Ascophillum nodosum, Laminaria japonica, Durvillea antarctica, Durvillea potatorum* and from the leaves of *Laminaria hyperborea*.

Preferably the compositions of the invention comprise Sodium alginates derived from *Laminaria hyperborea*.

Supplies of alginates having suitable mannuronic acid residue to guluronic acid residue ratios for carrying out the invention may be obtained from, for example, Pronova Biopolymer. Such a company supplies different grades of alginate which vary in, inter alia, molecular weight and viscosity.

Preferably, low viscosity grade sodium alginate is used to prepare the compositions of the invention. These are grades of sodium alginate for which the viscosity of a 10% weight/volume aqueous solution, when determined on a Brookfield RVT viscometer using spindle number 3 at 20 r.p.m. at 20° C., falls within the range 200–1500 cps.

The concentration of sodium alginate in the compositions of the invention should be higher than in conventional compositions, i.e. at least 8% w/v. Preferably the concentration is 9 to 20% w/v, more preferably 10 to 15% w/v and most preferably 10 to 11% w/v, especially around 10% w/v.

Further according to this aspect to the present invention there is provided a method of treating reflux oesophagitis, gastritis, dyspepsia or peptic ulceration which comprises the administration of a pharmacologically effective amount of an aqueous pourable liquid composition, comprising a) 8 to 15% w/v low viscosity sodium alginate, wherein the average mannuronic acid residue to guluronic acid residue ratio is at least 0.6:1; and b) 0.1 to 8% w/v alkali metal bicarbonate.

Further according to this aspect to the present invention there is provided a pharmaceutical composition for the treatment of reflux oesophagitis, gastritis, dyspepsia or peptic ulceration, or for use as a sustained releasing or targeted delivery composition, in the form of an aqueous pourable liquid comprising a) 8 to 15% w/v low viscosity grade sodium alginate, wherein the average mannuronic acid residue to guluronic acid residue ratio is at least 0.6:1; and b) 0.1 to 8% w/v alkali metal bicarbonate.

There is further provided a pharmaceutical composition for the treatment of reflux oesophagitis, gastritis, dyspepsia or peptic ulceration, or for use as a sustained releasing or targeted delivery composition, in the form of an aqueous pourable liquid comprising;

a) 8 to 15% w/v low viscosity grade sodium alginate, wherein the average mannuronic acid residue to guluronic acid residue ratio is at least 0.6:1;

b) 0.1 to 8% w/v alkali metal bicarbonate; and c) substantially no other suspending agents.

Turning now to the need for an alginate or alginic acid for forming an effective protective coating on gastrointestinal mucosa when brought into contact with same, it has now surprisingly been found that particular grades or types of alginates are able to interact much more effectively than others with components of the mucus of the gastrointestinal tract in order to provide a mucoadhesive coating. More especially, it has been found that these grades or types of alginate interact with mucin, a glycoprotein which is a major component of saliva and gastrointestinal mucus. The interaction of these alginates with mucin effectively strengthens the gel-like structure of the mucin thereby providing an effective mucoadhesive coating.

Therefore, according to a second aspect of the present invention there is provided an alginate or alginic acid having a mannuronic acid residue to guluronic acid residue ratio (M/G) of at least 1 for forming a protective coating on gastrointestinal mucosal tissue when brought into contact with same, preferably for use in the treatment of reflux oesophagitis, gastritis, dyspesia or peptic ulceration, and/or in sustained release or targeted delivery of an active.

According to a further aspect of the present invention there is provided a pharmaceutical composition for forming a protective coating on gastrointestinal mucosal tissue, preferably for use in the treatment of reflux oesophagitis, gastritis, dyspesia or peptic ulceration, and/or for as a sustained releasing or targeted delivery composition, the composition comprising an alginate or alginic acid having a mannuronic acid residue to guluronic acid residue ratio (M/G) of at least 1 for forming a protective coating on gastrointestinal mucosal tissue when brought into contact with same and a pharmaceutically acceptable carrier.

The pharmacetically acceptable carrier may, for example, be water, preferably deionised water.

Preferably, the composition of this aspect to the invention is also able to form a carbonated gelatinous foam or raft which floats on the stomach contents, in addition to forming a protective coating on the gastrointestinal mucosa.

Accordingly, there is provided a pharmaceutical composition for forming a protective coating on gastrointestinal mucosal tissue, preferably for use in the treatment of oesophagitis, gastritis, dyspepsia or peptic ulceration, and/or as a sustained releasing or targeted delivery composition comprising a) an alginate or alginic acid wherein the ratio of the mannuronic acid residues to the guluronic acid residues (M/G) is at least 1 for forming a protective coating on gastrointestinal mucosal tissue when brought into contact with same, and b) an alkali metal bicarbonate.

Advantageously, the composition further includes a polyvalent metal ion as a cross-linking agent, especially calcium or aluminium, most preferably calcium.

In a preferred embodiment of this aspect of the invention, the composition of the invention includes at least one high M alginate which is effective in forming a protective coating on the oesophageal mucosa and also at least one high G alginate in order to provide a carbonated gelatinous raft or foam of high strength.

Thus, in an embodiment of this aspect of the invention, there is provided a pourable liquid composition comprising i) from 1% to 10% (preferably 2.0% to 10%, more preferably 2.5% to 8%, especially 4% to 6%) in total of two or more alginates, of which from 10% to 90% comprises an alginate or alginic acid wherein the ratio of the mannuronic acid residues to the guluronic acid residues (M/G) is at least 1 for forming a protective coating on gastrointestinal mucosal tissue when brought into contact with same, and from 90% to 10% comprises an alginate or alginic acid wherein the ratio of the mannuronic acid residues to the guluronic acid residues (M/G) is not more than 2/3 in order to provide a carbonated gelatinous raft or foam of high strength, and ii) an alkali metal bicarbonate.

Preferably, the composition of this embodiment of the invention further comprises a polyvalent metal ion, (in particular calcium or aluminium and especially calcium) as a cross-linking agent.

It will be apparent to the person skilled in the art that in order to produce a pourable liquid composition the viscosity of the composition should not be too high. A suitable pourable composition may thus, for example include a relatively low amount of a viscous (high molecular weight) high M alginate and a relatively high amount of a less viscous (lower molecular weight) high G alginate. Similarly, a composition may suitably include a relatively high amount of a less viscous (lower molecular weight) high M alginate and a relatively low amount of a more viscous (higher molecular weight) high G alginate. Compositions not tending towards the above noted limits may also be suitable, such as for example a composition including approximately equal amounts of low viscosity high M and low viscosity high G alginates (provided that the M/G value is at least 1)

Where a liquid composition of the invention is not required to be pourable, a higher amount of total alginate (for example up to 20%) may be included.

In still another embodiment of this aspect of the invention, the compositions of the invention may also be provided in tablet or other solid unit dosage form. Thus according to this aspect of the invention there is provided a composition in solid unit dosage form comprising i) from 10% to 30% (preferably 15% to 25%, especially 20%) in total of two or more alginates, of which from 10% to 90% comprises an alginate or alginic acid wherein the ratio of the mannuronic acid residues to the guluronic acid residues (M/G) is at least 1 for forming a protective coating on gastrointestinal mucosal tissue when brought into contact with same, and from 90% to 10% comprises an alginate or alginic acid wherein the ratio of the mannuronic acid residues to the guluronic acid residues (M/G) is not more than 2/3 in order to provide a carbonated gelatinous raft or foam of high strength, and ii) an alkali metal bicarbonate.

In a further aspect to the present invention, there is provided a method of forming a protective coating on gastrointestinal mucosal tissue for treating reflux oesophagitis, gastritis, dyspepsia or peptic ulceration which comprises administering an orally effective amount of a composition including at least one alginate having a ratio of the mannuronic acid residues to the guluronic acid residues (M/G) of at least 1 for forming a protective coating on gastrointestinal mucosal tissue when brought into contact with same.

In a preferred embodiment of this aspect of the invention, the composition further comprises an alkali metal bicarbonate, and, advantageously, a polyvalent metal ion as a cross-linking agent. Preferably the polyvalent ion is calcium or aluminium, most preferably calcium.

In another preferred embodiment of this aspect of the invention, the composition comprises i) from 1% to 10% (preferably 2.0% to 10%, more preferably 2.5% to 8%, especially 4% to 6%) in total of two or more alginates, of which from 10% to 90% comprises an alginate or alginic acid wherein the ratio of the mannuronic acid residues to the guluronic acid residues (M/G) is at least 1 for forming a protective coating on gastrointestinal mucosal tissue when brought into contact with same, and from 90% to 10% comprises an alginate or alginic acid wherein the ratio of the mannuronic acid residues to the guluronic acid residues (M/G) is not more than 2/3 in order to provide a carbonated gelatinous raft or foam of high strength, and ii) an alkali metal bicarbonate.

In still a further aspect to the present invention there is provided the use of an alginate or alginic acid having a mannuronic acid residue to guluronic acid residue ratio (M/G) of at least 1 for forming a protective coating on gastrointestinal mucosal tissue when brought into contact with same, preferably for the treatment of reflux oesophagitis, gastritis, dyspesia or peptic ulceration, and/or for use in sustained release or targeted delivery of an active.

In a still further aspect of the invention there is provided the use of an alginate or alginic acid having a mannuronic acid residue to guluronic acid residue ratio (M/G) of at least 1 for the preparation of a medicament for the treatment of reflux oesophagitis, gastritis, dyspepsia or peptic ulceration by forming a protective coating on gastrointestinal mucosal tissue when brought into contact with same.

The interaction of alginates with mucin can be demonstrated Theologically by comparing the elastic, or storage, modulus (G') of the mucin with that of a mucin-alginate mixture.

Table 1 below shows the elastic modulus (G') of a range of sodium alginates of varying viscosity (and hence molecular weight) and varying M:G ratio in 2% aqueous solution. Also shown is the elastic modulus for a 2% aqueous solution of these alginates containing 15% partially purified porcine gastric mucin (type III Sigma Chemicals).

The G' values were determined using a Carri-med CSL 500 rheometer equipped with a 60 mm diameter cone and plate (angle 1.59 degrees) from frequency scans (0.01–10.0 Hz) at temperature 25° C. The values given are within the linear viscoelastic region of the samples and are those obtained at 5.3 Hz using a set displacement of $7.0 \times 10^{-4}$ rad.

The viscosity (Brookfield RVT Viscometer with spindle number 3 at 20 rpm at 20° C.) of a 1% solution of these alginates and the M:G ratio of each alginate are shown in table 2.

TABLE 1

Elastic modulus of alginates and alginate/mucin mixtures (G' for 15% mucin alone was 36)

| Sodium Alginate Grade | G' (2% Solution) | G' (2% Solution with 15% Mucin) |
|---|---|---|
| SF120 | 144 | 642 |
| SF/LF40 | 134 | 698 |
| SF200 | 143 | 640 |
| LF120L | 243 | 747 |
| SF60L | 260 | 6,124 |
| H120L | 243 | 1,059 |

TABLE 2

Viscosities and M:G ratios of alginate grade

| Sodium Alginate Grade | 1% Solution Viscosity (mpa.s) | M:G ratio |
|---|---|---|
| SF120 | 110 | 31:69 |
| SF/LF40 | 410 | 37:63 |
| SF200 | 990 | 31:69 |
| LF120L | 121 | 56:44 |
| SF60L | 368 | 56:44 |
| H120L | 950 | 54:46 |

It can be seen from tables 1 and 2 that the elastic modulus G' of 15% mucin (G'=36) is synergistically increased upon mixing with each alginate, but that the effect is increased in alginates with a M/G value of more than about 1 (high M). The effect is also increased greatly with higher viscosity, high M, alginates, whereas the effect is largely independent of the viscosity of high G alginates.

Thus, it is apparent the higher M alginates can interact more effectively with mucin in the gastrointestinal mucosa and that the resulting gel substance will form an effective protective coating on the gastrointestinal, in particular oesophageal and stomach, mucosa.

This formation of an effective protective coating on oesophageal mucosa by high M alginates is demonstrated as follows.

Table 3 shows the percentage cumulative alginate recovered after washing oesophageal mucosa with artificial saliva.

The values shown in Table 3 were arrived at by obtaining porcine oesophagus (the substrate) from an abattoir and cutting the substrate to a 15 mm width and a 90 mm length. Thereafter, the substrate was securely mounted on an inclined support, the angle of inclination of which was variable.

2% solutions of different grades of alginate were fluorescently labelled. Approximately 0.5 grams of the alginate solution was then applied to the substrate which was held at an angle of 180° (i.e. horizontal) and left for 5 minutes.

The alginate coated substrate was then inclined at a selected angle (76°) for 1 minute and any excess alginate solution allowed to flow off the inclined mounted substrate.

The substrate and alginate solution were then washed with an artificial saliva solution (0.27% porcine mucin type III (Sigma Chemicals) and a range of salts) at a rate of 1 ml per minute and the eluent collected at 3 minute intervals over a 30 minute period.

At all times the substrate and associated equipment were held under constant conditions of relative humidity (90%) and temperature (37° C.).

The collected eluate fractions were then analysed for alginate content using a fluorescence spectrophotometer.

The percentage cumulative alginate solution recovered can be used as an indicator of the bioadhesive nature of the alginate, given that a higher percentage cumulative alginate recovered implies a weaker adhesion and vice versa.

Table 3 below clearly indicates that the three alginate solutions showing the lowest percentage cumulative recovery (and therefore displaying the highest bioadhesion) are those having an M:G ratio of at least 1. (M:G ratios are given in Table 2)

TABLE 3

Percentage cumulative alginate recovered following washings with artificial saliva.

| Sodium Alginate Grade | Percentage Alginate Solution Recovered (%) | Ranking |
|---|---|---|
| SF/LF40 | 68.23 ± 6.4 | 4 |
| SF200 | 73.42 ± 3.4 | 5 |
| LF120L | 12.49 ± 1.8 | 1 |
| SF60L | 14.57 ± 1.1 | 2 |
| H120L | 32.12 ± 4.2 | 3 |

(n = 12)

Particularly advantageous mucoadhesive coatings can be achieved by using high viscosity, high M alginates. Thus, preferred formulations according to the invention can include a relatively small amount of a high viscosity high M alginate to provide good coating efficacy and a relatively large amount of a low M (high G) alginate to provide good raft strength, whilst also providing a composition which is pourable. Such formulations may preferably include from 10% to 30% (with respect to the total alginate) of at least one alginate having a M/G value of at least 1 and from 90% to 70% (with respect to the total alginate) of at least one alginate having a M/G value of not more than 2/3.

Also in a pourable composition, good raft strength may also be achieved by using a relatively small amount of a high viscosity high G alginate and a relatively large amount of low viscosity high M alginate may be used to achieve a good coating efficacy. Thus, further preferred compositions according to the invention may include from 70% to 90% (with respect to the total alginate) of at least one alginate having a M/G value of at least 1 and from 30% to 10% (with respect to the total alginate) of at least one alginate having a M/G value of not more than 2/3.

Where a high M alginate and a high G alginate are used each having a relatively lower viscosity, the amounts of each alginate (with respect to the total amount of alginate in the composition) may preferably be respectively from 40% to 60% and from 60% to 40%.

Furthermore, when a composition including a high M alginate is used to form an effective coating on the gastrointestinal mucosa, pharmaceutically active substances maybe incorporated in the composition, whereby targeted delivery and/or sustained release of the pharmaceutically active substance by absorption through the gastrointestinal mucosa can be achieved.

Thus, by means of the present invention there can be provided compositions able to form a protective coating on the mucosa of the oesophagus and stomach and further able to form a carbonated gelatinous raft or foam which, on reflux, precedes the stomach contents into the oesophagus. Because of their mucoadhesive properties, the compositions of the invention are able to form a protective coating on the oesophagus both when passing downwards through the oesophagus directly after ingestion and also when passing from the stomach in to the oesophagus on reflux. The compositions can also be effective in enhancing an existing coating, or re-coating the oesophagus, on reflux.

The compositions of the invention, because of their mucoadhesive properties which allow them to form an effective coating on the oesophageal or gastric mucosa, can be used as vehicles for targeted delivery of pharmaceutically active compounds. These may be compounds which act systemically and are absorbed into the body through the mucosa, such as the oesophageal mucosa, the stomach mucosa and in particular the intestinal mucosa. Particular active ingredients suitable for targeted delivery in or via the stomach include, for example, locally acting antimicrobial agents, H2-antagonists, pro-kinetic agents (such as cisapride), carbenoxolone, sucralfate, local anaesthetics, proton pump inhibitors or anticholinergic agents. Other compounds which are particularly suitable for targeted delivery by means of the compositions of the invention may include those beneficial in the treatment of gastric disorders, such as, for example compounds effective in the treatment of gastric lesions.

The mucoadhesive properties of the compositions of the present invention also render the compositions suitable for use as sustained releasing compositions, in particular for sustained release of pharmaceutically active ingredients through the stomach mucosa. By incorporation in the compositions of the invention of active ingredients suitable for sustained administration through the stomach mucosa, the mucoadhesive coating (and the carbonated gelatinous foam or raft) formed by the compositions may act as a reservoir of the active ingredient from which sustained release can occur.

Supplies of alginates having suitable mannuronic acid residue to guluronic acid residue ratios for carrying out the invention may be obtained from, for example, Pronova Biopolymer.

A suitable procedure to determine the ratio of mannuronic acid residues to guluronic acid residues in alginic acids is by nuclear magnetic resonance spectroscopy. Such a method is described in the paper by Hans Grasdalen et al (Carbohydrate Research 68 (1979) 2331). It should be noted that the hydrolysis method mentioned in that paper may be replaced by a two step hydrolysis carried out at pH 5.4, 100° C. for 1 hour followed by pH 3.8, 100° C. for 1 hour.

The concentration of alkali metal bicarbonate in the compositions of the invention is preferably 0.1 to 8% w/v, more preferably 0.5 to 5% w/v, even more preferably 1 to 3% w/v and most preferably 1.5 to 3% w/v. The alkali metal bicarbonate is preferably sodium or potassium bicarbonate or a mixture thereof. More preferably at least 90% (most preferably 100%) of the alkali metal bicarbonate is sodium bicarbonate.

Where the compositions of the invention comprise a suspending agent it may suitably be selected from xanthan gum, carageenans, hypromellose, tragacanth, pectin, pregelatinised potato starch, sodium starch glycolate, carbomer (eg Carbopol 934P or Carbopol 974P, BF Goodrich) or mixtures thereof. Where present the suspending agent is used in an amount of 0.01 to 1% w/v. When carbomer is used as a suspending agent, it is preferably to include a further basic ingredient in the composition to neutralise the suspending agent and to thereby increase its efficacy. Such a basic ingredient, for example, sodium hydroxide, is preferably included in a 1:1 (wt for wt) ratio with the carbomer.

However, it is a feature of the first aspect to the present invention that stable compositions may be prepared without the use of suspending agents. Thus it is preferred that no suspending agent is added to the compositions of the first aspect to the present invention.

As mentioned earlier, the compositions of the present invention preferably further comprise a source of divalent or trivalent metal ions to strengthen the raft formed in the stomach. These metal ions preferably become available when the compositions reach the stomach but must not be available before then (as the compositions will gel too early). Suitable metal ions are aluminium and, preferably, calcium ions. Most preferably the compositions comprise calcium carbonate.

The compositions of the present invention therefore preferably further comprise from 0.1 to 5% w/v calcium ions, more preferably 0.5 to 3.5% w/v calcium carbonate, most preferably 1.5 to 3% w/v.

The compositions of the present invention may further comprise preservatives to prevent contamination and subsequent deterioration by micro-organisms. Examples of suitable preservatives are ethyl and butyl para-hydroxybenzoates and their salts, which are preferably used in combination.

Preferred concentrations for the preservatives are 0.01 to 0.5% w/v.

The compositions of the present invention may also include one or more of the following ingredients, colours, sweeteners (e.g. sodium saccharin), flavours or pH adjusting agents (e.g. monopotassium phosphate or dipotassium phosphate). Preferably such ingredients are present in an amount of 0.01 to 1% w/v.

The compositions according the present invention may also contain conventional antacids including aluminium hydroxide, calcium carbonate, sodium bicarbonate, potassium bicarbonate, magnesium hydroxide, magnesium carbonate and magnesium trisilicate. Preferably such ingredients are present in an amount of from 1 to 15% w/v, preferably 2 to 8% w/v.

Where the compositions of the present invention are intended for use as sustained releasing compositions they will also contain active ingredients suitable for sustained administration in the stomach.

Where the compositions of the present invention are intended for use as targeted delivery compositions they will also contain active ingredients suitable for specific delivery to the stomach, for example locally acting antimicrobial agents, H2-antagonists, carbenoxolone, sucralfate, local anaesthetics, proton pump inhibitors, anticholinergic agents and/or prokinetic agents.

The dosage regime for the compositions of the invention will generally be up to 1000 mg total alginate up to four times daily. For a liquid composition comprising 5% total alginate, this equates to a regime of 20 ml four times daily. For a composition in tablet form, the tablet may suitably include 500 mg total alginate and the dosage will suitably be one to two tablets up to four times daily.

Amounts expressed herein as percentages are % w/v for liquid ingredients and % w/w for solid ingredients, unless otherwise specified.

The invention will now be illustrated by reference to the following examples.

EXAMPLE 1

A composition containing

| | |
|---|---|
| Sodium alginate LFR 5/60 RB | 100 g |
| (M:G ratio 0.9:1, Pronova Biopolymer) | |
| Sodium bicarbonate | 26 g |
| Calcium carbonate | 32 g |
| Monopotassium phosphate | 0.6 g |
| Dipotassium phosphate | 5.4 g |
| Ethyl parahydroxybenzoate | 2 g |
| Butyl parahydroxybenzoate | 0.2 g |
| Sodium saccharin | 1 g |
| Flavour | 0.7 g |
| Deionised water | to 1 liter | is made up as follows 1. 917 ml of deionised water are dispensed into a mixing vessel and cooled to approximately 20° C.
2. The monopotassium phosphate and dipotassium phosphate are added and stirred until dissolved.
3. The preservatives, carbonates and sweetener are added to the mixture and stirred for 5 minutes.
4. The alginate is added with stirring over a period of 3 minutes.
5. The mixture is stirred for 30 minutes (the flavour being added after 10 minutes).
6. The temperature is controlled during manufacture to 22° C. (plus or minus 5° C.).

EXAMPLES 2 TO 6

The following examples are all produced according to the method of Example 1 using the amounts of components as set out in the table below.

TABLE

| | EXAMPLE | | | | |
|---|---|---|---|---|---|
| | 2 | 3 | 4 | 5 | 6 |
| Sodium alginate LFR 5/60 (M to G ratio 0.45:1 Pronova Biopolymer) | 25 g | 25 g | 25 g | 25 g | 25 g |
| Sodium alginate LFR 5/60RB (M to G ratio 1.1:1 Pronova Biopolymer) | 75 g | 75 g | 75 g | 75 g | 75 g |
| Sodium Bicarbonate | 26 g | 26 g | 26 g | 16 g | 20 g |
| Calcium carbonate | 32 g | 16 g | 60 g | 32 g | 32 g |
| Potassium phosphate | 0.6 g | 0.6 g | 0.6 g | 0.6 g | 0.6 g |
| Dipotassium phosphate | 5.4 g | 5.4 g | 5.4 g | 5.4 g | 5.4 g |
| Ethyl para-hydroxybenzoate | 2.0 g | 2.0 g | 2.0 g | 2.0 g | 2.0 g |
| Butyl para-hydroxybenzoate | 0.2 g | 0.2 g | 0.2 g | 0.2 g | 0.2 g |
| Sodium saccharin | 1.0 g | 1.0 g | 1.0 g | 1.0 g | 1.0 g |
| Flavour | 0.7 g | 0.7 g | 0.7 g | 0.7 g | 0.7 g |
| Deionised water to | 1 ltr | 1 ltr | 1 ltr | 1 ltr | 1 ltr |

EXAMPLE 7

The following composition is prepared:

| | |
|---|---|
| Sodium Alginate LFR 5/60 | 25.0 g |
| (viscosity 1% = 6 mPa.s, M Content 36%) | |
| Sodium Alginate LF10L | 25.0 g |
| (Viscosity 1% = 9.5 mPa.s M Content 57%) | |
| Calcium Carbonate | 16.0 g |
| Sodium Bicarbonate | 26.7 g |
| Methyl Parahydroxybenzoate | 4.0 g |
| Propyl Parahydroxybenzoate | 0.6 g |

-continued

| | |
|---|---|
| Carbopol 974P | 6.5 g |
| Sodium Hydroxide | 3.0 g |
| Sodium Saccharin | 1.0 g |
| Flavour | 0.2 g |
| Deionised Water | to 1 liter |

The method of preparation is as follows:

1. The Carbopol 974P is dispersed in 450 ml deionised water and neutralised with the sodium hydroxide.
2. The sodium bicarbonate, calcium carbonate, parahydroxy benzoates and saccharin are mixed in a separate second vessel with 450 ml of deionised water.
3. The sodium alginates are added slowly to the second vessel and stirred until fully dissolved.
4. The contents of the second vessel are added to the Carbopol 974P phase and stirred until fully dispersed.
5. The flavour is added and stirred in.
6. The volume is adjusted to 1 liter by the addition of further deionised water and the mixture is stirred until this water is fully dispersed.

EXAMPLE 8

The following composition is prepared using the method of Example 1:

| | |
|---|---|
| Sodium Alginate LFR 5/60 | 40.0 g |
| (viscosity 1% = 6 mPa.s, M Content 36%) | |
| Sodium Alginate SF60L | 10.0 g |
| (Viscosity 1% = 368 mPa.s M Content 56%) | |
| Sodium Bicarbonate | 26.7 g |
| Calcium Carbonate | 16.0 g |
| Methyl Parahydroxybenzoate | 4.0 g |
| Propyl Parahydroxybenzoate | 0.6 g |
| Carbopol 974P | 1.0 g |
| Sodium Hydroxide | 0.46 g |
| Sodium Saccharin | 1.0 g |
| Flavour | 0.7 g |
| Deionised Water | to 1 liter |

EXAMPLE 9

The following composition is prepared using the method of Example 1:

| | |
|---|---|
| Sodium Alginate LFR 5/60 | 30.0 g |
| (viscosity 1% = 6 mPa.s, M Content 36%) | |
| Sodium Alginate LF120L | 20.0 g |
| (Viscosity 1% = 121 mPa.s M Content 56%) | |
| Potassium bicarbonate | 20.0 g |
| Calcium Carbonate | 10.0 g |
| Methyl Parahydroxybenzoate | 4.0 g |
| Propyl Parahydroxybenzoate | 0.6 g |
| Carbopol 974P | 2.0 g |
| Sodium Hydroxide | 0.92 g |
| Sodium Saccharin | 1.0 g |
| Flavour | 0.7 g |
| Deionised Water | to 1 liter |

EXAMPLE 10

The following composition is prepared:

| | |
|---|---|
| Sodium Alginate LFR 10/60 | 10.0 g |
| (viscosity 1% = 54 mPa.s, M Content 29%) | |
| Sodium Alginate SF60L | 15.0 g |
| (Viscosity 1% = 368 mPa.s M Content 56%) | |
| Sodium Bicarbonate | 13.3 g |
| Calcium Carbonate | 8.0 g |
| Ethyl Parahydroxybenzoate | 2.0 g |
| Butyl Parahydroxybenzoate | 0.2 g |
| Xanthan Gum | 4.0 g |
| Monopotassium Phosphate | 0.6 g |
| Dipotassium Phosphate | 5.4 g |
| Sodium Saccharin | 1.0 g |
| Flavour | 0.2 g |
| Deionised Water | to 1 liter |

The method of preparation is as follows:

1. The phosphates are dissolved with stirring in 900 ml of deionised water.
2. The sodium bicarbonate, preservatives and sodium saccharin are added and dispersed with stirring.
3. The Xanthan Gum is slowly added and dispersed with stirring for 20 minutes.
4. The alginates are slowly added and dispersed with stirring for a further 20 minutes.
5. The calcium carbonate is added in and stirred to disperse.
6. The flavour is added and stirred in.
7. The volume is adjusted to 1 liter by the addition of further deionised water and the mixture is stirred until this water is fully dispersed.

EXAMPLE 11

The following composition is prepared:

| | |
|---|---|
| Sodium Alginate LFR 5/60 | 40.0 g |
| (viscosity 1% = 6 mPa.s, M Content 36%) | |
| Sodium Alginate SF60L | 10.0 g |
| (Viscosity 1% = 368 mPa.s M Content 56%) | |
| Aluminum Hydroxide (as 10% gel) | 100.0 g |
| Xanthan Gum | 4.0 g |
| Sodium Bicarbonate | 26.7 g |
| Monopotassium Phosphate | 0.6 g |
| Dipotassium Phosphate | 5.4 g |
| Ethyl Parahydroxybenzoate | 2.0 g |
| Butyl Parahydroxybenzoate | 0.2 g |
| Sodium Saccharin | 1.0 g |
| Flavour | 0.7 g |
| Deionised Water | to 1 liter |

The method of preparation is as follows:

1. The phosphates, sodium bicarbonate, sodium saccharin and paraben preservatives are dissolved in 800 ml of deionised water.
2. The xanthan gum is added slowly and dispersed by stirring for 20 minutes.
3. The alginates are slowly added and dispersed with stirring for a further 20 minutes.
4. The aluminium hydroxide gel is added and stirred in.
5. The flavour is added and stirred in.
6. The volume is adjusted to 1 liter by the addition of further deionised water and the mixture is stirred until this water is fully dispersed.

What is claimed is:

1. An aqueous pourable liquid composition comprising from 8 to 15% w/v of sodium alginate and an alkali metal bicarbonate, wherein the sodium alginate has an average mannuronic acid residue to guluronic acid residue ratio of 0.7:1 to 1.3:1.

2. The composition according to claim 1 wherein at least 50% w/v of the sodium alginate has a mannuronic acid residue to guluronic acid residue ratio of greater than 0.8:1.

3. The composition according to claim 2 wherein
   from 70 to 80% w/v of the sodium alginate has a mannuronic acid residue to guluronic acid residue ratio of from 0.9:1 to 1.2:1, and
   from 20 to 30% w/v of the sodium alginate has a mannuronic acid residue to guluronic acid residue ratio of from 0.35:1 to 0.5:1.

4. A pharmaceutical composition in the form of an aqueous pourable liquid for the treatment of reflux oesophagitis, gastritis, dyspepsia or peptic ulceration, or for use as a sustained releasing or target delivery composition comprising:
   (i) from 8 to 15% w/v of low viscosity grade sodium alginate in which the average mannuronic acid residue to guluronic acid residue ratio is from 0.7:1 to 1.3:1, and
   (ii) from 0.1 to 8% w/v alkali metal bicarbonate, the composition including substantially no other suspending agents.

5. A method for treating reflux oesophagitis, gastritis, dyspepsia or peptic ulceration which comprises orally administering to a patient in need of such treatment an effective amount of an aqueous pourable liquid composition comprising:
   (i) from 8 to 15% w/v low viscosity sodium alginate wherein the average mannuronic acid residue to guluronic acid residue ratio is from 0.7:1 to 1.3:1, and
   (ii) from 0.1 to 8% w/v alkali metal bicarbonate.

6. A pharmaceutical composition for forming a protective coating on gastrointestinal mucosal tissue, said composition comprising:
   (i) an alginate component comprising an alginate or alginic acid having a mannuronic acid residue to guluronic acid residue ratio of at least 1 and an alginate or alginic acid having a mannuronic acid residue to guluronic acid residue ratio of not more than 2/3,
   (ii) an alkali metal bicarbonate, and
   (iii) a polyvalent metal ion as a cross-linking agent.

7. The composition according to claim 6 in which the crosslinking agent is aluminum or calcium.

8. The composition according to claim 6 in which the alginate component comprises (i) from 1% to 10% w/v of two or more alginates, of which from 10% to 90% w/v comprises an alginate or alginic acid having a mannuronic acid residue to guluronic acid residue ratio of at least 1 and from 90% to 10% w/v comprise an alginate or alginic acid having a mannuronic acid residue to guluronic acid residue ratio of not more than 2/3.

9. The composition according to claim 8 in which the alginate component is present in an amount of from 2.5% to 8% w/v.

10. The composition according to claim 8 in which the alginate component is present in an amount of from 4% to 6% w/v.

11. The composition according to claims 9 or 10 in which the cross-linking agent is aluminum or calcium.

12. The composition according to claim 11 which is in pourable liquid form.

13. The composition according, to claim 11 which is in solid-unit dosage form.

14. A pharmaceutical composition in solid unit dosage form comprising;
   (i) from 10% to 30% w/v of an alginate component having two or more alginates, of which from 10% to 90% w/v comprises an alginate or alginic acid having a mannuronic acid residue to guluronic acid residue ratio of at least 1 and from 90% to 10% w/v comprises an alginate or alginic acid having a mannuronic acid residue to guluronic acid residue ratio of not more than 2/3, and
   (ii) an alkali metal bicarbonate.

15. The composition according to claim 14 in which the alginate component is present in an amount of from 15 to 25% w/v.

16. A method for forming a protective coating on gastrointestinal mucosal tissue for treating reflux oesophagitis, gastritis, dyspepsia or peptic ulceration, which method comprises orally administering to a patient in need of such treatment an effective amount of a composition comprising (i) an alginate component comprising an alginate or alginic acid having a mannuronic acid residue to guluronic acid residue ratio of at least 1 and an alginate or alginic acid having a mannuronic acid residue to guluronic residue ratio of not more than 2/3.

17. The method according to claim 16 in which the composition further comprises (ii) an alkali metal bicarbonate, and (iii) a polyvalent metal ion as a cross-linking agent.

18. The method according to claim 17 in which the cross-linking agent is aluminum or calcium.

19. The method according to claim 16 in which the composition comprises:
   (i) from 1% to 10% w/v of an alginate component having two or more alginates, of which from 10% to 90% w/v comprises an alginate or alginic acid having a mannuronic acid residue to guluronic acid residue ratio of at least 1 and from 90% to 10% w/v of which comprises an alginate or alginic acid having a mannuronic acid residue to guluronic acid residue ratio of not more than 2/3, and
   (ii) an alkali metal bicarbonate.

* * * * *

UNITED STATES PATENT AND TRADEMARK OFFICE
CERTIFICATE OF CORRECTION

PATENT NO.   : 6,395,307 B1  Page 1 of 1
DATED        : May 28, 2002
INVENTOR(S)  : Douglas Banning et al.

It is certified that error appears in the above-identified patent and that said Letters Patent is hereby corrected as shown below:

<u>Title page,</u>
Item [73], Assignee should be changed as follows:
-- [73]   Assignee:       Reckitt Benckiser Healthcare (UK) Limited --

Signed and Sealed this

Thirty-first Day of December, 2002

JAMES E. ROGAN
*Director of the United States Patent and Trademark Office*